United States Patent [19]

Lindsay et al.

[11] 4,301,245

[45] Nov. 17, 1981

[54] CHROMOGENIC METHOD OF DETECTING ENDOTOXINS IN BLOOD

[75] Inventors: Gene Lindsay, Middletown; Andrew J. O'Beirne, Walkersville, both of Md.

[73] Assignee: Dynasciences Corporation, Los Angeles, Calif.

[21] Appl. No.: 154,360

[22] Filed: May 29, 1980

[51] Int. Cl.$^3$ .............................................. C12Q 1/44
[52] U.S. Cl. .................................... 435/4; 435/13; 435/19; 435/23; 435/188; 23/230 B
[58] Field of Search ................... 435/4, 13, 23, 24, 7, 435/259, 188, 19; 23/230 B; 424/95, 101; 252/408 R

[56] References Cited

U.S. PATENT DOCUMENTS

| | | | |
|---|---|---|---|
| 3,954,663 | 5/1976 | Yamamoto et al. | 435/13 |
| 4,038,147 | 7/1977 | Reno | 435/13 |
| 4,188,264 | 2/1980 | Iwanaga et al. | 435/19 |

FOREIGN PATENT DOCUMENTS 614050 1/1976 Switzerland .

OTHER PUBLICATIONS

Chem. Abstr., vol. 91: 205167k (1979).
Chem. Abstr., vol. 92: 82290f (1980).

*Primary Examiner*—Benoit Castel
*Attorney, Agent, or Firm*—Donald E. Nist

[57] ABSTRACT

An improved method is provided for detecting endotoxins in blood serum and/or plasma, particularly human blood fractions. The method employs king crab amebocyte lysate, preferably Limulus amebocyte lysate, in the presence of a substrate which has a selected colorimetric indicator bound to it. The indicator is capable of being split from the substrate by an enzyme which can be generated in the lysate by endotoxins in the blood. Thus, the endotoxins convert proenzyme in the lysate to the enzyme which effects the splitting off of the colorimetric indicator from the substrate. The endotoxin concentration in the blood can thus be determined colorimetrically, that concentration being proportional to the concentration of color indicator split from the substrate. The blood sample need not be extracted, as is required in prior methods, with a solvent such as chloroform to remove inhibitors therein which would interfere with a lysate gelation reaction. Heparin is utilized in the present method in a concentration sufficient to stabilize the lysate against loss of potency but insufficient to inhibit the reaction whereby endotoxin generates the described splitting enzyme from proenzyme in the lysate and the reaction of the enzyme to cause the split. The blood fraction need not be diluted with water and the lysate may be one which has been reconstituted from dry powder, if desired. The method is simple, highly effective, reproducible, inexpensive and rapid.

11 Claims, No Drawings

CHROMOGENIC METHOD OF DETECTING ENDOTOXINS IN BLOOD

BACKGROUND OF THE INVENTION

1. Field of the Invention

The present invention generally relates to a biological test method and more particularly to an improved method of measuring bacterial endotoxins in blood fractions, particularly human blood fractions, and an improved method of stabilizing king crab amebocyte lysate.

2. Prior Art

Various methods have been devised for the detection of bacterial endotoxins in human and animal blood. One of the newer methods involves the use of Limulus amebocyte lysate. In that method, the lysate is contacted with an endotoxin-containing source such as a human blood fraction which has been previously extracted with chloroform or the like or diluted substantially with water to reduce the concentration of an inhibitor in the blood to below the level which would substantially impair the desired gelation of the lysate by blood endotoxins. The previously diluted or purified blood fraction is mixed with the lysate and the endotoxins in the blood cause the lysate to form a clot.

Unfortunately, test results have varied widely, due to the variable nature of the lysate. However, advances have been recently made in the purification of the lysate to improve the test results. See for example, U.S. Pat. No. 4,107,077 wherein a member of a selected group of organic solvents is utilized to extract inhibitors from the lysate in order to improve the sensitivity of the lysate to blood endotoxins. The firmness and extent of the clot formed by the gelation reaction is measured subjectively in this test by viewing the same, in some cases while inverting the tube containing the clot. Therefore, a true quantitative determination of the concentration of endotoxin cannot be made utilizing this method. Moreover, the method requires skilled personnel, is not always accurate, and takes a considerable length of time to perform, of the order of 45-90 minutes.

Bacterial endotoxins are produced by Gram negative bacteria, many of which are very dangerous or deadly in human beings and animals. Symptoms range from mild to high fever and in many cases death results. It is extremely important in order to promptly initiate the proper medical treatment to identify as soon as possible the fact that endotoxins are present in the blood fraction sample and, if possible, the concentration of the endotoxins. The previously described gelation reaction test method is deficient because of the considerable length of time necessary to carry it out, because it does not accurately measure endotoxin concentration, because it is difficult to standardize and because it requires highly skilled experienced personnel to perform it.

A new chromogenic substrate method for assaying bacterial endotoxins using Limulus amebocyte lysate is described in pages 209-220 of "Biomedical Applications of the Horseshoe Crab" (1979) Allen R. Lis, Inc. That method is specified as not being applicable to blood and blood fractions because of the inhibitors in the blood. Instead, the disclosure is directed to the testing of bacterial solutions containing endotoxins such as might be the case, for example, in testing food for contamination. German Auslegeschrift No. 27 40 323 discloses a similar process to the one described in the above-indicated literature reference. The test specimens utilized in the disclosure in the Auslegschrift are solutions derived from bacterial sources other than blood. Such procedures have not been utilized in testing for blood endotoxins.

It would therefore be highly desirable to be able to provide an improved method of determining bacterial endotoxins in human and animal blood. Such method should be rapid, reproducible, simple to conduct and inexpensive and should preferably result in a quantitative determination of endotoxin concentration. It would also be highly desirable if the method could employ standardized measuring equipment utilizable by relatively unskilled personnel.

It has also been found that, although lyophilized lysate retains its potency under suitable storage conditions whenever liquid king crab amebocyte lysates are used, whether original or reconstituted from the powder form, they tend to deteriorate in potency rapidly. Thus, their reactivity to bacterial endotoxins sharply and progressively decreases with time before and during tests. Accordingly, variable test results are a common occurrence, especially when utilizing liquid lysates of different ages. It would therefore be highly desirable if a method could be devised to improve the stability of the liquid lysates in order to increase the accuracy of tests involving their use.

SUMMARY OF THE INVENTION

The present invention satisfies all of the foregoing needs. Thus, an improved method of detecting the presence and concentration of bacterial endotoxins in human and animal blood is provided. The method is substantially as set forth in the Abstract above. It involves reacting a human or animal blood serum and/or plasma fraction which may contain bacterial endotoxin with king crab amebocyte lysate, specifically Limulus amebocyte lysate, and a selected substrate which contains a bound colorimetric indicator capable of being split from the substrate by an enzyme which can be generated in the lysate by the endotoxin. Thus, the endotoxin is capable of converting proenzyme in the lysate to the desired enzyme. The concentration of colorimetric indicator split from the substrate by the enzyme can be colorimetrically measured in standard equipment and is directly proportional to the concentration of endotoxin in the blood fraction being tested.

It has been determined that chromogenic substrates of the type, for example, which are disclosed in U.S. Pat. No. 4,028,318 are suitable for use as the chromogenic substrate in the present method. Such substrates are represented by the general formula:

$$R_1-A_1-A_2-Gly-Arg-NH-R_2$$

or its salts, where $R_1$ is hydrogen or alkanoyl having from 1 to 12 carbon atoms or cyclohexylcarbonyl or benzoyl or benzoyl substituted with one or two halogen atoms, methylamine or phenyl groups or benzene sulphonyl or toluenesulphonyl, $R_2$ is nitrophenyl or naphthyl or nitronaphthyl or methoxynaphthyl or quinolyl or nitroquinolyl, $A_1$ is a single bond or one of the amino acids Gly, Ala, Val, Leu, Ileu, Pro, Met, Phe or Tyr, and $A_2$ is one of the amino acids Glu, Gln, Asp, or Asn. Other substrates such as are disclosed in Volume 29, pages 209-220, (1979) of Progress In Clinical And Biological Research may be employed.

It has been found that it is unnecessary to purify the human or animal blood fraction to remove inhibitors of a gelation reaction between the lysate and blood endotoxin in order to carry out the present method. Nor is it necessary to greatly dilute the blood fraction to reduce the inhibitor concentration to below an effective level. At least one of these procedures has been necessary heretofore whenever Limulus amebocyte lysate has been used to detect bacterial endotoxins.

A method has also been found to prevent a decrease in potency, that is a decrease in effectiveness, of the lysate. The method involves the use of a selected concentration of heparin. That concentration is enough to accomplish the stabilization of the lysate but insufficient to inhibit the endotoxin-lysate reaction which generates the colorimetric indicator-splitting enzyme. Such heparin concentration normally is in the range of about 0.1–0.4 standard units of heparin per milliliter of the lysate, where the lysate contains 15–25 mg of lysate (on a dry basis) therein.

With the present method, it is possible to conduct the desired endotoxin test within a 15 minute period, including mixing of the ingredients, allowing them to react and making the colorimetric determination. This 15-minute period is much shorter than that required for previous test methods for bacterial endotoxins. Moreover, the present method simply and accurately measures the concentration of the endotoxin to indicate the extent of the Gram negative bacterial infection. Further features are set forth in the following detailed description.

DETAILED DESCRIPTION

A human or animal blood sample is tested in accordance with the present method. Although a whole blood sample could be used, the color of the blood would tend to interfere with the colorimetric reading so that it is preferred that the blood utilized be a fraction such as blood serum and/or blood plasma. This fraction need not be treated in any way, such as by heating, or by diluting it with water or by extracting it with an organic solvent such as chloroform to remove or reduce the concentration of inhibitors in the blood which would interfere with a gelation reaction with the king crab amebocyte lysate. Previous chromogenic methods for detecting endotoxin have been indicated as inapplicable to blood because of the presence of such inhibitors and/or have indicated that purification of the blood to remove or reduce the inhibitor concentration would be required. Nevertheless, it has been discovered that such purification or dilution is not necessary in the present method.

In carrying out the present method, the blood sample which preferably is a human blood sample, although the method is applicable to animal blood samples, is mixed with a king crab amebocyte lysate, preferably Limulus amebocyte lysate. However, lysate from other forms of horseshoe crabs such as Tachypleus tridentatus, the Japanese horseshoe crab, can be used. The lysate can be prepared in accordance with conventional procedures. Procedures such as are disclosed in Journal of Clinical Investigation, Volume 51, July 1972, Bulletin of Johns Hopkins Hospital, Volume 115, pages 265–274 (1964) and Proceedings of the Society for Experimental Biochemical Medicine, Volume 137, pages 334–342, can be used to recover the lysate. Briefly, the conventional procedure usually involves withdrawing crab blood by sterile needle from the crab heart, placing the blood into a mixture which prevents aggregation of the blood cells and premature lysis of the cells, separating the amebocytes from the remainder of the blood by centrifugation, lysing the amebocytes by mechanical breaking, freeze-thawing or by osmotic lysis in pyrogen-free distilled water in a volume ratio of water to cells of about 3-6:1 or the like. The lysate thus obtained is centrifuged free of the broken cells and usually freeze dried, that is, lyphophilized to preserve it. When it is ready for use, the lysate powder is diluted with approximately 50 volumes of sterile pyrogen-free distilled water to bring it to a solids concentration per ml. of about 0.02 gm. In the present method, lysate is used which may either be one freshly prepared or one which has been preserved, usually in lyophilized powder form, and which has been reconstituted or which during the preparation of the reaction mixture is directly added as a powder to the liquid mixture. In any event, the lysate is present in a solids concentration in the reaction mixture of about 1.50 to about 2.50 gm/100 ml.

The substrate utilized in the present method contains a selected colorimetric indicator capable of being split off from the substrate by lysate enzyme produced by conversion of proenzyme by endotoxin in the blood sample. For such purposes, any suitable substrate generally of the type described in, for example, U.S. Pat. No. 4,028,318 can be utilized. However, certain of such substrates have been found to be more advantageous than others. In this regard, a substrate characterized by the general formula Bz—Ile—Glu—Gly—Arg—pNA is preferred. This substrate comprises benzoyl-isoleucine-glutamic acid-glycine-arginine-p-nitroanilide. Another suitable substrate is acetate-isoleucine-glutamic acid-glycine-arginine-p-nitroanilide. A third useful substrate is benzoyl-valine-glycine-arginine-p-nitro-analide. Further suitable substrates can easily be determined by minimal experimental testing. Such substrates may contain, for example, 2-naphthyl-amide as the color indicator instead of the p-nitroanilide.

In accordance with the present method, the desired test reaction is effected by mixing together the blood fraction sample, the amebocyte lysate and the selected substrate in suitable relative concentrations. In carrying out the method human blood serum can, for example, be added to a reaction zone such as a sterile test tube, can then be diluted with about five to ten volumes of pyrogen-free sterile water and powdered Limulus amebocyte lysate or other king crab amebocyte lysate in a concentration of about 1.50 to about 2.50 gram/100 ml. can then be added to each such test tube. Each test tube is supplied with 0.1 ml. of the lysate solution. The temperature of each test tube is preferably kept within a suitable range, for example, 35°–40° C., most preferably about 37° C. This mixture is thoroughly mixed together and incubated for about 7–9 minutes, preferably about 8 minutes.

The substrate is then added to each test tube, preferably in a relative concentration of about four to six, most preferably about five, volumes per volume of undiluted serum. The resulting mixture is then mixed together and incubated for about 2–4 minutes, preferably about 3 minutes, at the desired previously indicated temperature of about 37° C. for a total reaction time (initial incubation plus final incubation) of approximately 10–12 minutes, preferably about 11 minutes, whereupon acetic acid, for example, 1 N, is added to each test tube in a volume sufficient to stop the reaction from continuing, usually 100 µl. The mixture is then left in each test tube and read on a colorimeter at 405 nM. The concentration of the endotoxin is calculated from a standard curve previously prepared from known dilutions of a standard endotoxin.

It has been found that the reaction rate, that is the rate at which the splitting of the color indicator from the substrate occurs, increases linearly with increasing concentration of endotoxin in the 0.01–0.1 ng per ml. range.

Further details are indicated in the Examples below:

EXAMPLE I

A human serum sample suspected of containing endotoxin from E. Coli gram negative bacteria is diluted with 10 volumes of steril pyrogen-free water and 100 $\mu$l thereof is added to a sterile pyrogen-free test tube. Limulus amebocyte lysate reconstituted from the lyophilized powder in pyrogen-free sterile water to a solids weight concentration of about 2 gram/100 ml. is added in a 100 $\mu$l volume to the same test tube, and the mixture is incubated at 37° C. for 8 minutes. 500 $\mu$l of benzoyl-isoleucine-glutamic acid-glycine-arginine-p-nitroanilide color indicator is then added to the test tube and stirred into the mixture for 3 minutes at 37° C., whereupon 100 $\mu$l of 50% acetic acid is added to the test tube and the mixture is immediately read in a colorimeter at 405 nm. The reading is 0.5 O.D. This reading is compared with a standard curve previously prepared from known dilutions of a known concentration of endotoxin, sufficient lysate to provide the enzyme color splitting as previously described, and the same color indicator. The reading indicates the presence of endotoxin in a concentration of 0.05 ng/ml., establishing the presence of E. Coli bacterial infection and an indication of its severity.

In a parallel test, the same human blood serum is used but in a 10 $\mu$l undiluted amount added to 200 $\mu$l of lysate at one-half of the usual concentration, i.e., about 1 gm/100 ml. The other test parameters are held the same. The test results are comparable. So are test results using two-fold and four-fold dilutions of the serum. The only effect dilution of the serum has on the test is to change the sensitivity of detection of the test, greater dilutions increasing the minimal amount of endotoxin concentration which is detectable. At a 1:10 dilution of sample in water, the normal detection limit of 0.01 ng of endotoxin is changed to 0.1 ng/ml.

EXAMPLE II

The method of Example I, first test, is followed, except that the substrate is acetate-isoleucine glutamic acid-glycine arginine-p-nitro-anilide used in a 500 $\mu$l concentration. The same results as were obtained in Example I are found using the same human serum as used in Example I. A reading of 0.5 at 405 nm is obtained in a colorimeter, indicating the presence of the endotoxin in a concentration of about 0.05 ng/ml.

Comparable results are obtained in a parallel test substituting benzoyl-valine-glutamic acid-glycine-arginine-p-nitroanilide as the substrate listed above in this Example.

IMPROVED LYSATE SENSITIVITY

Inasmuch as the king crab amebocyte lysate tends to lose sensitivity over a period of time commencing with its reconstitution from the powder or from its original preparation, it is desirable to find a way of restoring that sensitivity and/or preventing its decrease. The sensitivity loss is characterized by a gradual reaggregation of an active component in the lysate and a decreased response to endotoxin. When a series of tests are run utilizing lysate or when a single test is run by a method which requires the use of lysate over an extended period of time such as one or more hours, noticeable decreases in lysate sensitivity occur and contribute to a decrease in the accuracy and effectiveness of any test employing the lysate.

However, it has now been found that the addition of small amounts of heparin to the lysate reverses or prevents the loss of sensitivity. At high concentrations of heparin, the heparin inhibits the lysate reaction with endotoxin and therefore such high concentrations of heparin must be avoided. However, just below the level where all such inhibition ceases, the heparin stabilizes the lysate against loss of sensitivity. The range of effectiveness of the heparin has been determined to be about 0.1–0.8 standard units of heparin per ml. of the lysate, where the lysate has a concentration on a dry solids basis of about 1.5 to 2.5 gm/100 ml. A standard unit of heparin is defined in the Pharmacopoeia of the United States of America as the minimum quantity of USP sodium heparin which, when added to 0.8 ml. of saline T.S., maintains fluidity in one ml. of prepared plasma for one hour after the addition of 0.2 ml of calcium chloride solution (1% volume concentration).

No other means have been found to be effective to stabilize the lysate against loss of sensitivity. It will be understood that this method of stabilizing the lysate is useful in various types of applications including but not limited to the improved chromogenic method of the present invention. The following example illustrates the improved effects obtained through the use of heparin-stabilized lysate in comparison with unstabilized lysate in the chromogenic method of the present invention.

EXAMPLE III

A first sample was formed by reconstituting one ml of lyophilized Limulus amebocyte lysate (2 gm/100 ml.) with 1 ml of pyrogen-free sterile water containing 0.1 units of heparin. A second sample was formed by adding together 1 ml of the same lyophilized Limulus amebocyte lysate as was used in the first sample but reconstituted with 1 ml of pyrogen-free sterile water containing no heparin.

In parallel tests, 0.1 ml of each sample was then mixed in a sterile pyrogen-free test tube with 0.1 ml of 0.05 mg per ml standard endotoxin and was incubated therein at 37° C. for 10 minutes. In each case, 0.5 ml of the same colorimetric indicator substrate utilized in Example I was added with stirring to the test tube and the resultant mixture was incubated for an additional 3 minutes, whereupon 0.1 ml to 50% acetic acid was then added to each solution to stop the reaction. The color of the resulting solution was in each case read at 405 nM in a colorimeter over a water blank. The same procedure was repeated each hour for eight hours to determine the extent of loss of sensitivity of the heparin stabilized samples in comparison with the unstabilized samples.

It was determined that in the case of the heparin stabilized samples, an initial optical density of about 0.74 remained substantially constant for approximately four hours and decreased only slightly to about 0.70 over the remaining 4 hours. In contrast, the unstabilized samples had an initial optical density of 0.62 which decreased to 0.60 in one hour, further decreased to about 0.50 in three hours and by the end of the 8th hour had declined to 0.30.

The test results clearly indicate that the heparin stablilized lysate samples had better sensitivity initially and that the sensitivity remained substantially constant throughout an 8 hour period, whereas the unstabilized lysate samples exhibited a decline in sensitivity almost immediately and that the sensitivity by the end of the 8th hour was less than 50% of the initial sensitivity of the samples. Accordingly, it is clear that introduction of the heparin into the lysate enables the lysate to be used over a long period of time without impairment of lysate sensitivity and without producing fluctuating test results, which interfere with an accurate quantitative determination of endotoxin levels.

Various other changes, modifications, alterations and additions can be made in the methods of the present invention, their steps and parameters. All such changes, modifications, alterations and changes as are within the scope of the appended claims form part of the present invention.

What is claimed is:

1. An improved chromogenic method of detecting endotoxins in blood, which method comprises:
   a. reacting an untreated blood fraction sample which comprises serum and/or plasma with king crab amebocyte lysate and a selected substrate containing a selected colorimetric indicator capable of being split from said substrate by an enzyme, said reaction being carried out for a time sufficient to cause any endotoxin present in the blood fraction to effect the generation in the lysate of enzyme capable of splitting off said colorimetric indicator from said substrate and to cause said splitting to occur; and,
   b. thereafter determining said endotoxin concentration colorimetrically, said endotoxin concentration being proportional to the concentration of said color indicator split from said substrate.

2. The improved chromogenic method of claim 1 wherein said endotoxin converts proenzyme in said lysate to said enzyme and wherein said blood is human blood.

3. The improved chromogenic method of claim 2 wherein said blood sample contains a sufficient concentration of blood inhibitors to the gelation reaction which normally occurs between said lysate and endotoxin which may be present in said blood sample so as to substantially inhibit said gelation reaction.

4. The improved chromogenic method of claim 2 wherein said blood sample is essentially undiluted with water.

5. The improved chromogenic method of claim 2 wherein said lysate is Limulus amebocyte lysate and contains an amount of heparin sufficient to stabilize said lysate against loss of potency but insufficient to inhibit said endotoxin-lysate reaction, said amount of heparin being present in a concentration of at least about 0.1 and less than 0.8 units per milliliter of said lysate.

6. The improved chromogenic method of claim 5 wherein said heparin concentration is about 0.1–0.4 unit per milliliter of said lysate.

7. The improved chromogenic method of claim 5 wherein said lysate has been reconstituted from dry powder.

8. The improved chromogenic method of claim 7 wherein said heparin has been added to said lysate after said lysate has been reconstituted.

9. The improved chromogenic method of claim 5 wherein said heparin is in the form of an ammonium salt thereof.

10. A method of stabilizing king crab amebocyte lysate against loss of potency, said method comprising combining with said lysate an amount of heparin sufficient to stabilize said lysate against loss of potency but insufficient to inhibit the reaction between said lysate and endotoxins, said amount of heparin being present in a concentration of at least about 0.1 and less than 0.8 units per milliliter of said lysate.

11. The method of claim 10 wherein said heparin concentration is about 0.1–0.4 units per milliliter of said lysate.

* * * * *